(12) United States Patent
Kasza et al.

(10) Patent No.: US 7,389,653 B2
(45) Date of Patent: Jun. 24, 2008

(54) MEDICAL ICE SLURRY PRODUCTION DEVICE

(75) Inventors: Kenneth E. Kasza, Palos Park, IL (US); John Oras, Des Plaines, IL (US); HyunJin Son, Naperville, IL (US)

(73) Assignee: The University of Chicago, Chicago, IL (US)

( * ) Notice: Subject to any disclaimer, the term of this patent is extended or adjusted under 35 U.S.C. 154(b) by 283 days.

(21) Appl. No.: 11/229,060

(22) Filed: Sep. 15, 2005

(65) Prior Publication Data
US 2007/0056313 A1    Mar. 15, 2007

(51) Int. Cl.
*F25D 17/02* (2006.01)
(52) U.S. Cl. .......................... 62/342; 62/434
(58) Field of Classification Search ............... 62/342, 62/434, 435, 68
See application file for complete search history.

(56) References Cited

U.S. PATENT DOCUMENTS

| | | | |
|---|---|---|---|
| 2,800,456 A | 7/1957 | Shepherd | |
| 3,069,866 A | 12/1962 | Dunn | |
| 3,180,110 A | 4/1965 | Dunn | |
| 3,255,600 A | 6/1966 | Mitchell et al. | |
| 3,425,419 A | 2/1969 | Dato | |
| 3,504,674 A | 4/1970 | Swenson et al. | |
| 3,987,211 A | 10/1976 | Dunn et al. | |
| 3,998,070 A * | 12/1976 | Mueller | 62/393 |
| 4,111,209 A | 9/1978 | Wolvek et al. | |
| 4,416,281 A | 11/1983 | Cooper et al. | |
| 4,474,016 A | 10/1984 | Winchell | |
| 4,526,012 A * | 7/1985 | Chigira | 62/196.3 |
| 4,540,501 A | 9/1985 | Ternes et al. | |

(Continued)

FOREIGN PATENT DOCUMENTS

JP        11-335660        12/1999

OTHER PUBLICATIONS

"Computer Codes: COMMIX-1AR/P," Reactor Analysis and Enginerring, http://www.rae.anl.cov/codes/commix, printed on Apr. 15, 2003.

(Continued)

*Primary Examiner*—William E Tapolcai
(74) *Attorney, Agent, or Firm*—Brinks Hofer Gilson & Lione

(57) ABSTRACT

The present invention relates to an apparatus for producing sterile ice slurries for medical cooling applications. The apparatus is capable of producing highly loaded slurries suitable for delivery to targeted internal organs of a patient, such as the brain, heart, lungs, stomach, kidneys, pancreas, and others, through medical size diameter tubing. The ice slurry production apparatus includes a slurry production reservoir adapted to contain a volume of a saline solution. A flexible membrane crystallization surface is provided within the slurry production reservoir. The crystallization surface is chilled to a temperature below a freezing point of the saline solution within the reservoir such that ice particles form on the crystallization surface. A deflector in the form of a reciprocating member is provided for periodically distorting the crystallization surface and dislodging the ice particles which form on the crystallization surface. Using reservoir mixing the slurry is conditioned for easy pumping directly out of the production reservoir via medical tubing or delivery through other means such as squeeze bottles, squeeze bags, hypodermic syringes, manual hand delivery, and the like.

14 Claims, 3 Drawing Sheets

U.S. PATENT DOCUMENTS

| | | | |
|---|---|---|---|
| 4,596,120 A | 6/1986 | Knodel et al. | |
| 4,605,006 A | 8/1986 | Jacques | |
| 4,745,922 A | 5/1988 | Taylor | |
| 4,750,336 A | 6/1988 | Margen | |
| 4,838,039 A | 6/1989 | Knodel | |
| 4,872,866 A | 10/1989 | Davis | |
| 4,914,921 A | 4/1990 | Knodel | |
| 5,065,598 A | 11/1991 | Kurisu et al. | |
| 5,088,487 A | 2/1992 | Turner | |
| 5,218,828 A | 6/1993 | Hino | |
| 5,262,055 A | 11/1993 | Bae et al. | |
| 5,281,215 A | 1/1994 | Milder | |
| 5,415,222 A | 5/1995 | Colvin et al. | |
| 5,457,962 A * | 10/1995 | Faries et al. | 62/68 |
| 5,502,980 A * | 4/1996 | Faries et al. | 62/342 |
| 5,505,055 A | 4/1996 | Franklin, Jr. | |
| 5,514,094 A | 5/1996 | Anello et al. | |
| 5,709,654 A | 1/1998 | Klatz et al. | |
| 5,722,482 A | 3/1998 | Buckley | |
| 5,755,756 A | 5/1998 | Freedman, Jr. et al. | |
| 5,807,318 A | 9/1998 | St. Goar et al. | |
| 5,833,688 A | 11/1998 | Sieben et al. | |
| 5,837,003 A | 11/1998 | Ginsburg | |
| 5,902,299 A | 5/1999 | Jayaraman | |
| 5,916,242 A | 6/1999 | Schwartz | |
| 5,950,438 A * | 9/1999 | Faries et al. | 62/72 |
| 6,012,298 A | 1/2000 | Goldstein | |
| 6,126,684 A | 10/2000 | Gobin et al. | |
| 6,148,634 A * | 11/2000 | Sherwood | 62/434 |
| 6,179,831 B1 | 1/2001 | Bliweis | |
| 6,244,052 B1 | 6/2001 | Kasza | |
| 6,270,493 B1 | 8/2001 | Lalonde et al. | |
| 6,312,452 B1 | 11/2001 | Dobak et al. | |
| 6,500,172 B1 | 12/2002 | Panescu et al. | |
| 6,533,804 B2 | 3/2003 | Dobak, III et al. | |
| 6,547,811 B1 | 4/2003 | Becker et al. | |
| 6,649,040 B1 * | 11/2003 | Mirchi et al. | 205/390 |
| 6,679,906 B2 | 1/2004 | Hammack et al. | |

OTHER PUBLICATIONS

Search Report and Written Opinion for PCT/US2007/035857.

* cited by examiner

MEDICAL ICE SLURRY PRODUCTION DEVICE

FEDERALLY SPONSORED RESEARCH OR DEVELOPMENT

The United States Government has rights in this invention pursuant to Contract No. W-31-109-ENG-38, between the United States Department of Energy and the University of Chicago.

BACKGROUND

The present invention relates to an apparatus for producing medical grade, highly fluid, sterile ice slurry capable of being delivered at high ice particle loadings through specially designed medical delivery tubing and insertion devices. Appropriate slurry delivery tubing and insertion devices are described in co pending patent application Ser. No. 11/038,570 entitled "Phase-Change Particulate Ice Slurry Coolant Medical Delivery Tubing and Insertion Devices" filed on Jan. 1, 2005, the entire teaching of which is incorporated herein by reverence.

Inducing hypothermia has been used as a technique for improving neurological and cardiovascular function following medical emergencies such as cardiac arrest, stroke, myocardial infarction, and the like. Cooling an organ reduces its metabolic demand, which dramatically enhances the ability of cells to survive severe oxygen deprivation, ischemia. Application of phase change particulate ice slurries to targeted organs has proved to be an effective method of inducing protective hypothermia. For example, U.S. Pat. No. 6,547,811 and pending U.S. patent application Ser. No. 10/162,442 filed Jun. 3, 2002 both entitled "Method of Inducing Hypothermia," and both incorporated herein by reference, teach the use of ice slurry to cool parts of the body in order to induce protective hypothermia during for example medical emergencies. Recently the application of protective organ cooling has been expanded to surgical procedures and other medical uses. For example, co-pending patent application Ser. No. 11/140,500 entitled "Ice Slurries and Method Using," filed May 27, 2005, the teaching of which is also incorporated herein by reference, discloses a number of applications where induced hypothermia through targeted cooling of various organs provides significant medical benefits. In the surgical setting, inducing hypothermia to counter the damaging effects of ischemia provides a viable option for protecting targeted organs, such as the brain, heart, kidneys, liver, or pancreas against oxygen deprivation resulting from obstructions in blood flow.

According to the invention describe in the "Ice Slurries and Method of Using" patent application, hypothermia is induced in targeted organs by delivering a two phase ice slurry directly to the targeted organ via specially designed tubing and injection devices. Because of the inherently higher amount of energy required to melt ice (heat of fusion for phase change 80 cal/g) rather than to warm chilled water (1 cal/g° C.), the cooling capacity of highly loaded ice slurry is many times greater than that of conventional chilled single-phase saline coolants. This reduces both the volume of coolant and the amount of time necessary to cool organs to the desired temperature. Furthermore, once fully melted in the body, ice slurry resembles basic medical-grade saline solution with a standard 0.9% salt concentration.

In order to successfully deliver the ice slurry to the targeted organs or other areas of the body the slurry itself must possess a number of important characteristics. First, the ice particles within the slurry must be small (<0.1 mm) and relatively smooth. Rough dendritic particles tend to become tangled up with one another leading to clogging in the delivery tubing or the insertion devices. Secondly, the saline solution from which the slurry is produced must be biologically compatible and sterile. Medical drip bag saline is preferred. The ice slurry must also be highly fluid and easily pumpable to avoid plugging delivery tubing and pumps. And finally, in order to achieve the most efficient cooling with a minimal amount of slurry, to avoid over loading of organs and other subsystems with coolant, high ice particle loading concentrations are desirable.

The present invention provides an apparatus and method for efficiently producing medical grade ice slurries for cooling targeted organs and other areas of the body.

SUMMARY OF THE INVENTION

The present invention relates to an apparatus for producing sterile ice slurries for medial applications. The apparatus is capable of producing highly loaded slurries suitable for delivery to targeted internal organs of a patient, such as the brain, heart, kidneys, lungs, stomach, pancreas and others, through medical size diameter tubing. Delivering such slurries to targeted organs can induce protective cell hypothermia or localized cooling during medical emergencies such as cardiac arrest or stroke or in medical procedures such as minimally invasive laparoscopic surgery, or organ harvesting for protection against ischemia.

According to an embodiment of the invention an ice slurry production apparatus includes a slurry production reservoir adapted to contain a volume of saline solution. An ice formation crystallization surface comprised of an elastic flexible membrane is provided within the slurry production reservoir. The membrane crystallization surface is chilled to a temperature below the freezing point of the saline solution within the reservoir such that ice particles form on the crystallization surface. A deflector in the form of a reciprocating member is provided for periodically distorting the membrane crystallization surface and dislodging the ice particles which form on the crystallization surface before they have a chance to become large aggregates of many particles.

In another embodiment a medical ice slurry production system includes a cooling tank. A refrigeration unit is provided for cooling an anti-freeze coolant (or any other type of refrigerant) and circulating the anti-freeze (refrigerant) through the cooling tank. A cold heat transfer plate is associated with the cooling tank. An ice slurry production reservoir including a deformable membrane crystallization surface is placed adjacent and in direct contact with the cold heat transfer plate. The ice slurry production reservoir is adapted to receive a volume of saline solution. A deflector is provided for periodically distorting the membrane crystallization surface to dislodge ice particles forming on the crystallization surface.

Finally, a method of producing ice slurry is provided. The method includes providing an ice slurry production reservoir having a deformable crystallization surface. Chilling the crystallization surface to a temperature below the freezing point of the saline solution such that ice particles form on the crystallization surface. And periodically deforming the crystallization surface to dislodge the ice particles therefrom. Once the slurry has reached the desired high ice loading concentration it may be pumped from the reservoir for medical cooling use.

Other systems, methods, features and advantages of the invention will be, or will become, apparent to those with skill in the art upon examination of the following figures and detailed description. It is intended that all such additional systems, methods, features and advantages be included within this description, be within the scope of the invention, and be protected by the following claims.

DETAILED DESCRIPTION OF THE DRAWINGS AND THE PRESENTLY PREFERRED EMBODIMENTS

Figure 1:
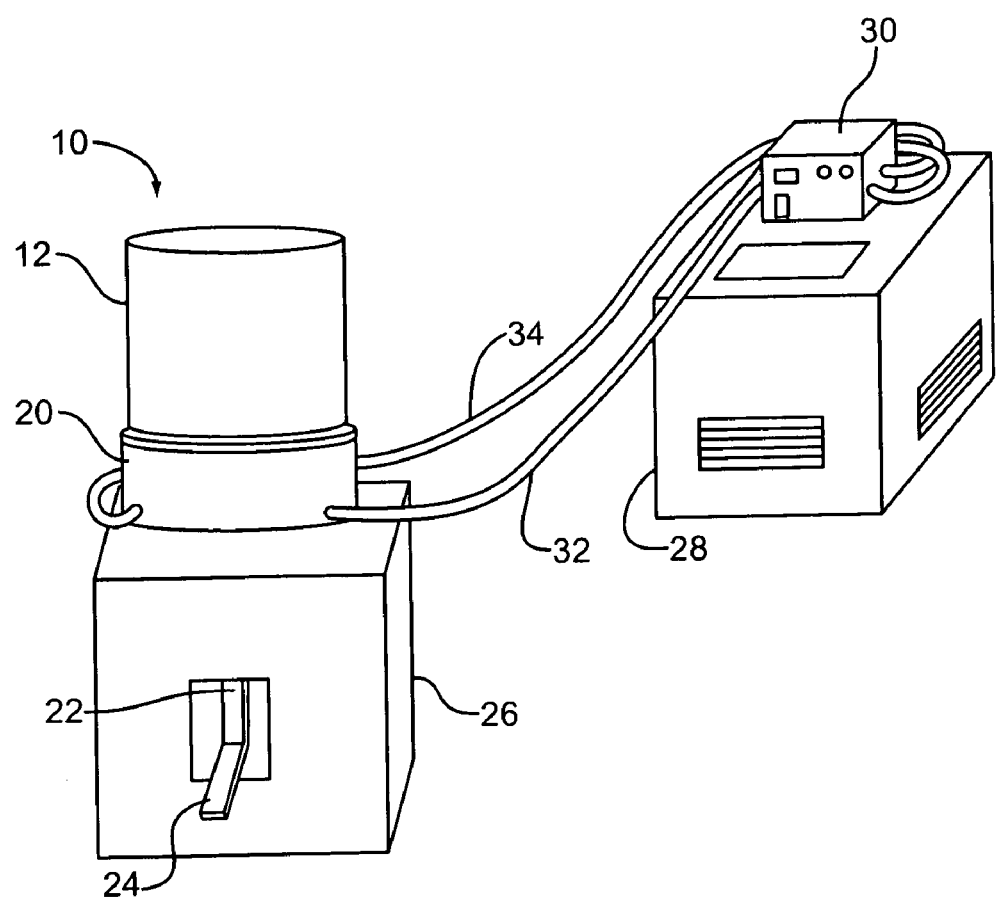
FIG. 1 is a three dimensional representation of a medical ice slurry production device according to the invention.
Figure 2:
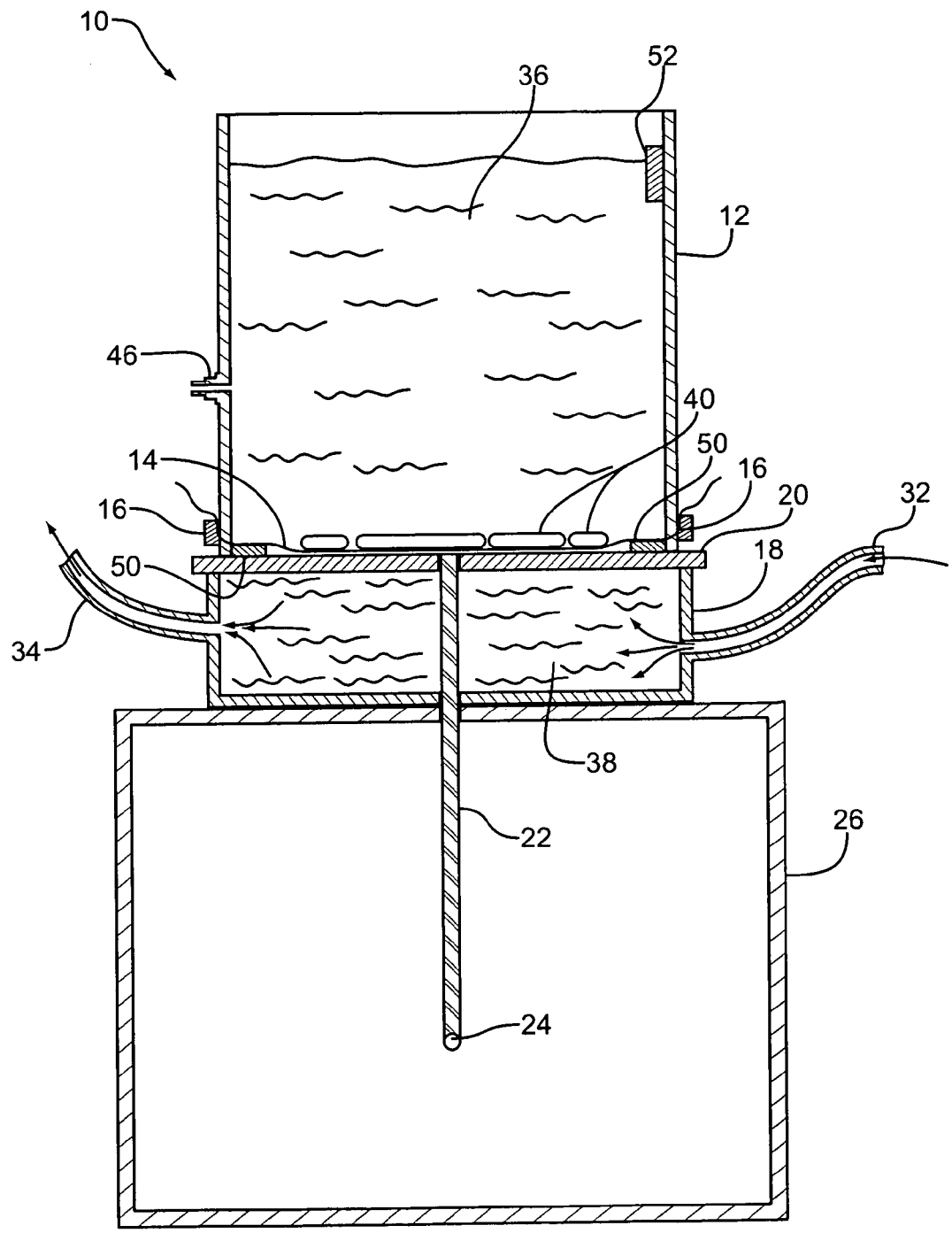
FIG. 2 is cross section of a medical ice slurry production device showing a reciprocating member in a first, withdrawn position.
Figure 3:
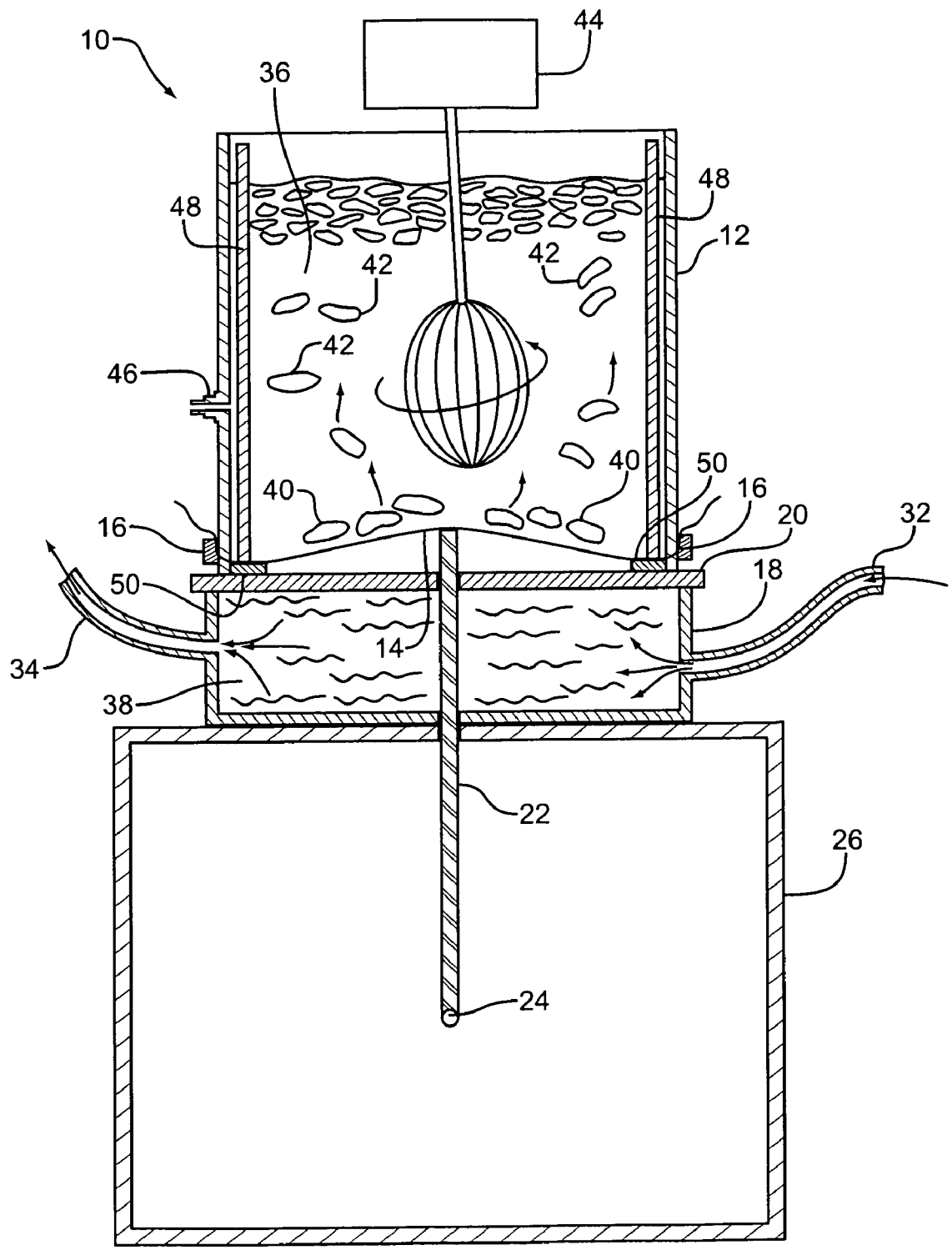
FIG. 3 is cross section of a medical ice slurry production device showing a reciprocating member in a second, extended position.

An embodiment of ice slurry production apparatus 10 is shown in FIG. 1. FIGS. 2 and 3 show cross sectional views of an ice slurry production reservoir and various internal components of the ice slurry production apparatus 10. The following description of the construction and operation of the slurry production apparatus will rely on all three figures. The various components shown in all three figures are labeled consistently throughout.

An ice slurry production apparatus 10 includes an ice slurry production reservoir 12. The ice slurry production reservoir 12 may be formed from a large polycarbonate cylinder capable of holding 3-4 liters or more of medical grade sterile saline solution. A foam and aluminized bubble thermal insulation covering may be provided to cover the ice slurry production reservoir 12 to speed the production of slurry and maintain the slurry after production for later use by minimizing heat gain from the surroundings. The ice slurry production reservoir 12 sits atop a copper cooling tank 18. The copper cooling tank 18 in turn sits atop a support base 26. A refrigeration unit 28, such as a Brinkman RK20 refrigeration system, is provided to chill a propylene glycol coolant 38 or other anti-freeze coolants. Other types of refrigeration may also be used. The refrigeration unit 28 circulates the coolant through the copper cooling tank 18 via a coolant supply tube 32 and a coolant return tube 34. Temperature controls 30 on the refrigeration unit 28 allow a technician to select the temperature of the coolant supplied to the copper cooling tank 18. Preferably a cooling temperature of about −27° C. or other cooling temperature below the freezing point of the saline solution 36 is maintained.

A cold heat transfer plate 20 separates the ice slurry production reservoir 12 and its saline solution contents from the copper cooling tank 18. The bottom of the slurry production reservoir 12 is covered by a thin flexible plastic membrane 14. The thin flexible plastic membrane, best seen in FIG. 3, is stretched across the bottom of the polycarbonate cylinder that forms the ice slurry production reservoir 12 and is clamped to the sides of the cylinder by a circular clamp 16, forming a seal. The plastic membrane 14 contacts the cold transfer plate 20 on top of the cooling tank 18.

A reciprocating member in the form of a manually operated steel rod 22 is provided which extends upward through the support base, through the cooling tank 18 and through the cold heat transfer plate 20. A handle 24 attached to the rod 22 extends through the side of the support base 26 so that the rod may be manually moved up and down in a reciprocating motion. Preferably the range of motion of the steel rod is limited to about 3.5 cm. When the rod 22 is withdrawn, i.e. when the rod is moved into the lower position as shown in FIG. 2, the membrane 14 stretched across the bottom of the ice slurry production reservoir 12 lies substantially flat in direct contact across the upper surface of the cold heat transfer plate. When the rod 22 is extended upward, as shown in FIG. 3, it engages the membrane 14, stretching and deflecting the membrane in the manner shown. Instead of the manually operated rod, an automated device, such as a motorized cam follower, a push type electrical solenoid, or the like may be provided for periodically engaging and distorting the shape of the flexible membrane 14.

When the slurry production reservoir is filled with saline solution 36 and the copper cooling tank is cooled to a temperature below the temperature of the saline solution, a heat exchange occurs between the saline solution and the cooling tank. The cold heat transfer plate 20 transfers cold from the cooling tank through the plastic membrane 14 to the saline solution within the ice slurry production reservoir 12. When the temperature of the saline solution is lowered down to its freezing point small ice particles 40 begin nucleating at random sites on the membrane 14. Because of the salt content of the solution 36 the ice particles 40 do not freeze solidly, but remain soft and mushy. During this freezing process the reciprocating rod 22 is raised and lowered periodically every 2 to 4 seconds. When the reciprocating rod is raised to the upper position as shown in FIG. 3, the flexible plastic membrane 14 is deflected and distorted, shucking or dislodging the ice particles 40 from the membrane. The shucked ice particles have a lower density than the remaining solution and float upward toward the surface of the solution where they collect at the top of the slurry production reservoir 12. Over time the slurry production reservoir 12 fills with ice particles to very high volumetric loading levels.

When the reciprocating rod 22 is extended to the upward position as shown in FIG. 3, the periphery of the flexible membrane is deformed to a much lesser extent than the more inward portions of the membrane. Accordingly, ice particles formed at the edge of the membrane 14 may not be dislodged when the rod 22 deforms the membrane. This can cause undesirably large ice particles to form along the bottom edge of the reservoir. To prevent this, a small ring of insulating foam 50 having a width of about 1.5 cm, for example, may be placed on the cold transfer plate 20 concentrically with the walls of the ice slurry production reservoir. The insulating foam ring prevents ice particles from forming or at least reduces the number of ice particles that form at the edges of the flexible membrane 14.

A mixer 44 may be provided to mix the slurry, breaking up any large ice platelets and conditioning the slurry particles to form a fluid slurry. The mixer 44 may be, for example, a Cole-Parmer Stir-Pak mixer. A 7 cm or 8 cm diameter paddle wheel mixer blade 42 having a height of 5-9.5 centimeters may be used to mix the slurry. The mixer blade may be tilted at various angles (including vertical) to the axis of the ice slurry production reservoir 12 in order to ensure thorough mixing of the slurry particles and preventing the creation of undesirable stagnant pools of unmixed slurry within the reservoir. Further, flow disruption tubes 48 may be installed vertically within the ice slurry production reservoir 12 in order to further enhance mixing. The flow disruption tubes 48 may reduce the vortex mixing pattern and cause greater vertical agitation of the slurry, yielding more effective mixing. It may be desirable to employ the mixer 42 at a slow speed throughout the slurry production and delivery process. Alternatively, it may be desirable to initiate mixing, at a slower or faster rate after a significant amount of ice has formed in the reservoir.

As the water component of the saline solution freezes into ice particles on the membrane and the concentration of ice in the reservoir increases, the concentration of salt remaining in the liquid phase rises, causing the temperature of the saline solution to drop further (freezing point depression). Loadings have been experimentally determined by calorimetry and compared to loading estimates determined based on the temperature of the slurry. It has been established that ice loading of the slurry mixture may be based on the freezing point depression of the saline solution as the ice loading increases. For example, at a target slurry temperature of −0.9° C., the calculated ice loading is 41.3%, a value which is in good agreement with calorimetry measurements made on actual slurry.

Accordingly, a thermocouple 52 may be provided within the slurry production reservoir 12 to monitor the temperature of the solution. The temperature of the solution may be used as an indication of the amount of ice that has formed in the reservoir, providing an accurate estimate of the ice loading concentration of the slurry. A target temperature may be established corresponding to a desired loading concentration. The slurry production process may be considered "finished" when the slurry temperature drops to the target value, indicating that the desired loading concentration has been reached. The ice slurry machine described above routinely and reliably produces 4 L batches of ice slurry at greater than 44% ice loading in less than 2 hours. The slurries are easily pumpable through the small delivery tubing and specially made injector tips associated with medical ice slurry cooling. The device features can be scaled up or down to produce smaller or larger batches of slurry as necessary.

After the mixing and conditioning process a medical delivery tube may be fitted over a slurry outlet port 46, and the slurry can be pumped from the reservoir 12 using a peristaltic tubing roller pump, such as a MasterFlex Easy-Load II pump using 5 mm-diameter insulated Saint-Gobain 3350 silicon tubing connected to for example a modified Cook 9.0 French RCF-9.0-38-J catheter. Delivery modes other than pumping may also be used for delivering the slurry to a targeted area on a patient. For example, slurry may be loaded into squeeze bottles, flexible squeeze bags or hypodermic needle syringes for delivery to a patient. Under sterile conditions the ice slurry can be hand scooped out of the reservoir for conventional hand application to an organ if direct access to the organ is available.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

The invention claimed is:

1. A medical ice slurry production system comprising:
   a cooling tank;
   a refrigeration unit for cooling a refrigerant and circulating the refrigerant through the cooling tank;
   a cold transfer plate associated with the cooling tank;
   an ice slurry production reservoir including a deformable ice crystallization surface adjacent the cold transfer plate the reservoir adapted to contain a saline solution; and
   a deflector for distorting the crystallization surface to dislodge ice particles forming on the crystallization surface.

2. The system of claim 1 wherein the ice crystallization surface comprises a flexible membrane stretched across a potion of the bottom of the ice slurry reservoir.

3. The system of claim 1 wherein the ice crystallization surface comprises a surface of the ice slurry production reservoir adjacent to and in direct contact with the cold heat transfer plate.

4. The system of claim 2 wherein the deflector comprises a reciprocating member adapted to engage and deform the flexible membrane periodically.

5. The system of claim 4 wherein the reciprocating member comprises a manually operated rod.

6. The system of claim 4 wherein the reciprocating member comprises an electro/mechanically activated member.

7. The system of claim 1 further comprising a mixer for mixing the slurry within the slurry reservoir for maintaining a fluid slurry.

8. An ice slurry production apparatus comprising:
   a slurry production reservoir adapted to contain a volume of a saline solution;
   a crystallization surface within the slurry production reservoir chilled to a temperature below a freezing point of the saline solution such that ice particles form on the crystallization surface;
   a deflector for distorting the crystallization surface and dislodging the ice particles formed on the crystallization surface;
   a cold heat transfer plate chilled to a temperature below the freezing point of the saline solution contained in the slurry production reservoir, the slurry production reservoir arranged such that the crystallization surface is located adjacent to and in direct contact with the cold heat transfer plate; and
   a refrigeration unit for chilling a refrigerant to a temperature below the freezing point of the saline solution located in the slurry production reservoir and circulating the refrigerant through a cooling tank, the cold heat transfer plate being associated with the cooling tank.

9. The apparatus of claim 8 wherein the crystallization surface comprises a flexible membrane.

10. The apparatus of claim 9 wherein the deflector comprises a reciprocating member adapted to engage and deform the flexible membrane periodically.

11. The apparatus of claim 10 wherein the reciprocating member comprises a manually operated rod.

12. The apparatus of claim 10 wherein the reciprocating member comprises an electro/mechanically activated member.

13. The apparatus of claim 8 further comprising a mixer for mixing the slurry within the slurry production reservoir for maintaining a fluid slurry.

14. The apparatus of claim 8 wherein the refrigerant is propylene glycol.

* * * * *